United States Patent [19]

Taylor et al.

[11] 4,083,882
[45] Apr. 11, 1978

[54] PRODUCTION OF 1,4-BUTANEDIOL

[75] Inventors: Paul D. Taylor, Clinton; Thomas H. Vanderspurt, Gillette, both of N.J.

[73] Assignee: Celanese Corporation, New York, N.Y.

[21] Appl. No.: 717,810

[22] Filed: Aug. 26, 1976

[51] Int. Cl.$^2$ .................... C07C 29/14; B01J 23/58
[52] U.S. Cl. ................. 260/635 R; 260/638 B; 260/635 A; 260/601 R; 252/473
[58] Field of Search .......... 260/635 R, 635 A, 638 B, 260/635 E

[56] References Cited

U.S. PATENT DOCUMENTS

| 2,763,696 | 9/1958 | Finch et al. | 260/638 B |
|---|---|---|---|
| 3,109,865 | 11/1963 | Foreman | 260/638 B |
| 3,239,570 | 3/1966 | Slaugh et al. | 260/635 R |
| 3,530,190 | 9/1970 | Olivier | 260/635 R |
| 3,859,369 | 1/1975 | Copelin | 260/635 R |
| 3,941,851 | 3/1976 | Smith | 260/635 R |

OTHER PUBLICATIONS

Kita et al. (I), Chem. Abst., vol. 79, pp. 401, #65782g, (1973).
Murai et al., Chem. Abst., vol. 77, pp. 344, #125962m, (1972).
Kita et al. (II), Chem. Abst., vol. 79, pp. 468, #339192, (1972).

*Primary Examiner*—James O. Thomas, Jr.
*Assistant Examiner*—James H. Reamer

[57] ABSTRACT

This invention provides an improved process for converting acrolein into 1,4-butanediol via allyl alcohol and 4-hydroxy-butanal intermediates.

12 Claims, No Drawings

PRODUCTION OF 1,4-BUTANEDIOL

BACKGROUND OF THE INVENTION

Ethylene glycol is an important constituent of commercial polyester resins. Also of increasing importance as resin constituents are higher polyols such as 1,4-butanediol. The development of new and improved commercial processes for production of higher polyols is under active investigation.

1,4-Butanediol can be derived from succinic acid, maleic anhydride and other four-carbon organic species, but such methods are not economically attractive. Another method of producing 1,4-butanediol is by the reaction of formaldehyde and acetylene to form 1,4-butynediol as an intermediate, which is subsequently hydrogenated to the desired 1,4-butanediol product.

Other investigators have endeavored to convert acrolein into 1,4-butanediol by subjecting acrolein to hydroformylation conditions, the objective being the formation of succinaldehyde as an intermediate product. The results have been unsatisfactory since the main conversion product recovered from acrolein under hydroformylation conditions is propionaldehyde.

Other efforts to produce 1,4-butanediol have involved hydroformylation of allyl alcohol to yield 4-hydroxybutanal as an intermediate which is subsequently hydrogenated to 1,4-butanediol. The liquid phase hydroformylation of allyl alcohol in the presence of hydroformylation catalysts such as cobalt carbonyl produces significant quantities of propanal, propanol and 2-methyl-3-hydroxypropanal as by-products, in addition to the desired 4-hydroxybutanal.

In U.S. Patent Office Defensive Publication No. 904,021 (Nov. 21, 1972) there is disclosed an improved hydroformylation process for converting unsaturated alcohols into diols. In one embodiment the Publication process involves the hydroformylation of allyl alcohol with rhodium-phosphine complex catalyst to produce a reaction mixture which is subsequently hydrogenated to yield 63 percent 1,4-butanediol and 25 percent 2-methylpropanediol. based on the weight of allyl alcohol charged. For the purposes of economic feasibility, higher conversion yields of 1,4-butanediol from allyl alcohol are desirable for commercial scale operations.

Accordingly, it is a main object of the present invention to provide an improved process for converting acrolein into 1,4-butanediol.

It is another object of the present invention to provide a catalyst for converting acrolein into allyl alcohol in a yield of at least 70 percent.

It is another object of the present invention to provide 4-hydroxybutanal in high yield as an intermediate product in a commercially feasible process for converting acrolein into 1,4-butanediol.

Other objects and advantages shall become apparent from the accompanying description and examples.

DESCRIPTION OF THE INVENTION

One or more objects of the present invention are accomplished by the provision of a process for producing 1,4-butanediol which comprises (1) reacting acrolein with hydrogen in the vapor phase in the presence of a catalyst comprising a silver-cadmium alloy, wherein the atomic ratio of silver to cadmium in the alloy is in the range between about 0.1 and 3 to 1, to yield a hydrogenation product mixture containing allyl alcohol; (2) contacting the allyl alcohol product mixture with hydrogen and carbon monoxide under hydroformylation conditions to yield a product mixture containing 4-hydroxybutanal; (3) separating the 4-hydroxybutanal from the product mixture; and (4) hydrogenating the 4-hydroxybutanal to produce 1,4-butanediol.

Acrolein To Allyl Alcohol

Several methods ae known in the prior art for converting $\alpha,\beta$-olefinically unsaturated carbonylic compounds into the corresponding $\alpha,\beta$-olefinically unsaturated alcohols.

British Pat. No. 734,247 and U.S. Pat. No. 2,763,696 disclose a process whereby acrolein may be converted to allyl alcohol by means of a vapor phase hydrogenation process. According to this process, moderate yields of allyl alcohol are obtained when acrolein is treated with free hydrogen in the vapor phase at a temperature between 210° C and 240° C in the presence of a catalyst comprising cadmium and one or more heavy metals of groups I, II, VI and VIII of the periodic table. Relatively high pressures are employed in the process on the order of 20 to 50 kilograms per square centimeter.

German Pat. No. 858,247 discloses a somewhat different process which is also useful for the conversion of acrolein to allyl alcohol. According to the German patent, good yields of allyl alcohol are obtained by reacting acrolein with free hydrogen in the presence of a catalyst containing cadmium oxide and a metal hydrogenating component which is preferably copper. The patent teaches that the best results are obtained when the process is operated at high temperatures and at high pressures on the order of 100–300 atmospheres.

U.S. Pat. No. 3,686,333 describes a liquid phase hydrogenation process for converting alkenals into alkenols in the presence of a catalyst mixture of a cadmium salt of a fatty acid and a transition metal salt of a fatty acid.

Japanese Pat. No. 73-01,361 discloses a process for hydrogenating $\alpha,\beta$-olefinically unsaturated aldehydes into the corresponding allylic alcohol derivatives. The efficiency of the process is improved by the recycle of by-products to the hydrogenation zone, or by passage of the by-products stream into a second hydrogenation zone. The preferred catalysts are mixtures of cadmium and copper, cadmium and silver, cadmium and zinc, cadmium and chromium, copper and chromium, and the like. The Japanese patent states that under steady state conditions 1.5 moles/hour of acrolein are converted to 1.05 moles/hours of allyl alcohol annd 0.4 mole/hour of n-propanol.

For the purposes of the present invention process, it has been found that acrolein can be converted into allyl alcohol with a conversion of at least 95 weight precent and a yield of at least 70 weight percent by the use of a novel catalyst comprising a silver-cadmium alloy on a carrier substrate.

In the practice of step (1) of the invention process, the acrolein and hydrogen at elevated temperature and pressure are passed in vapor phase through a reaction zone containing a silver-cadmium alloy catalyst which has exceptional selective hydrogenation activity.

The reaction temperature of the hydrogenation process can vary in the range between about 0° C and 300° C, and preferably between about 75° C and 250° C, and most preferably between about 100° C and 215° C.

The pressure of the hydrogenation process can vary in the range between about 15 and 15,000 psi, and preferably between about 75 and 5000 psi, and most preferably between about 250 and 2500 psi.

The mole ratio of hydrogen to acrolein in the vapor phase feed stream can vary in the range between about 1:1 and 1000:1. The preferred mole ratio of hydrogen to acrolein in the feed stream is in the range between about 5:1 and 200:1, and the most preferred mole ratio is in the range between about 10:1 and 150:1.

The rate at which the vapor phase gas stream is contacted with the silver-cadmium alloy catalyst is not critical, and can be varied consonant with the other processing conditions to achieve an optimal balance of conversion and yield parameters. The flow rate of feed gas reactants can vary over a broad range between about a total of 10 moles and 1000 moles of feed gas reactants per liter of catalyst per hour. In the case of acrolein, a preferred flow rate of feed gas reactants is one which provides a catalyst contact time between about 0.1 and 50 seconds. By the invention process, acrolein can be converted to allyl alcohol in step (1) with a space-time yield of greater than 900 grams per liter of catalyst per hour.

The process step (1) can be conducted either by passing the feed mixture through a fixed catalyst bed, or through a reactor wherein the catalyst is present in finely divided form and is maintained in a fluidized state by the upward passage there through of the gaseous reactants. The process step (1) is most conveniently carried out in a continuous manner, although intermittent types of operation can be employed. In a preferred method of continuous operation, the components of the feed stream are brought together and under the desired pressure are passed in vapor phase through the catalyst heated to the desired temperature. The reaction zone advantageously is an elongated tube or tubes containing the catalyst. The feed can be brought into contact with the catalyst in either the unheated or preheated condition. The effluent from the reactor can then be separated into its various constituents by conventional means, the most convenient of which is fractional distillation. If desired, any unconverted portion of the acrolein present in the effluent from step (1) can be recirculated through the catalyst in the reactor, preferably admixed with fresh feed gases.

The preferred selective hydrogenation catalyst for process step (1) is a silver-cadmium alloy on a carrier substrate, wherein the atomic ratio of silver to cadmium in the alloy is in the range of between about 0.1 and 3 to 1.

The carrier substrate can be selected from silica, Celite, diatomaceous earth, Kieselguhr, alumina, silica-alumina, titanium oxide, pumice, carborundum, boria, and the like. It is highly preferred that the silver-cadmium alloy be supported on a silica and/or alumina carrier substrate. The quantity of carrier substrate in the catalyst composition can vary in the range of between about 5 and 99.5 weight percent, based on the total catalyst weight.

The highly preferred catalysts are prepared by coprecipitating hydroxides of silver and cadmium from an aqueous solution of calculated quantities of water-soluble salts of silver and cadmium. The precipitation is effected by the addition of caustic to the aqueous solution.

The carrier substrate component of the catalyst composition can be incorporated during the catalyst preparation by preferably slurrying the finely divided carrier substrate mass in the said aqueous medium immediately after the silver-cadmium hydroxides are precipitated. Finely divided porous materials such as fumed silica or diatomaceous earth are highly preferred carrier substrate materials for the preparation of the present invention catalysts.

After the coprecipitation of silver-cadmium hydroxides has been accomplished, the solids phase is recovered by filtration or other conventional means. The filtered solids are washed with chlorine-free water until essentially neutral. For the purposes of a fixed bed operation, the dried filter cake preparation is calcined at a temperature between about 175° C and 300° C for a period of about two to twenty or more hours, and then the calcined material can be ground and pelleted. Prior to use the catalyst pellets can be reduced in a stream of hydrogen at a temperature between about 50° C and 250° C for a period of about 5 hours. For a fluidized bed operation, the calcined catalyst preparation can be ground and sized in a conventional manner to satisfy process design requirements. The reduction of the catalyst can also be accomplished in situ during the vapor phase hydrogenation process.

There are several critical aspects of catalyst preparation which must be respected in order to achieve a hydrogenation catalyst having unique and advantageous properties in comparison to prior art catalysts for selective hydrogenation of acrolein to allyl alcohol.

Firstly, the silver-cadmium alloy in the catalyst must contain an atomic ratio of silver to cadmium in the range between about 0.1 to 3 to 1, and preferably between about 0.4 and 2.2 to 1.

Secondly, the silver and cadmium in the catalyst must be in the free metal state, and must be substantially in the form of an alloy, i.e., X-ray diffraction spectra should confirm the absence of unalloyed silver or cadmium crystals. Preferred silver-cadmium alloy catalysts are solid solutions which nominally exhibit an X-ray diffraction pattern which is substantially free of detectable unalloyed metal crystallite lines.

In terms of X-ray diffraction data as more fully described hereinbelow, a preferred silver-cadmium alloy catalyst can consist substantially of $\alpha$-phase silver-cadmium, with detectable splitting of X-ray diffraction lines which is indicative of silver-rich and/or cadmium-rich $\alpha$-phase crystallites. Silver-cadmium catalysts which also have outstanding selectivity for high yield conversion of acrolein-type compounds into allyl alcohol-type compounds are those in which the alloy composition consists of more than about 50 percent of $\gamma$-phase silver-cadmium crystallites as characterized by X-ray diffraction pattern.

Thirdly, it has been found that the production of silver-cadmium alloy catalysts which exhibit the greatest selectivity for converting acrolein to allyl alcohol, can be achieved if the coprecipitation step of the catalyst preparation is conducted within restricted limitations and under controlled conditions. Thus, the total concentration of the water-soluble salts (e.g., nitrate salts) in the aqueous solution should be maintained in the range between about 5 weight percent, and the solubility limit of the salts, and the quantity of caustic added as a precipitating agent should approximate the stoichiometric amount within narrow limits. It is particularly advantageous to employ a water-soluble hydroxide (e.g., an alkali metal hydroxide) as the caustic precipitating agent, and to add the caustic rapidly with stirring to facilitate formation of a precipitate of fine crystals or gel. Excellent results are obtained, for example, if 17 grams of silver nitrate and 34 grams of cadmium nitrate are dissolved in 200 milliliters of water, and 18 grams of potassium hydroxide are dissolved in 200 milliliters of water and both solutions are added rapidly and simultaneously to 100 milliliters of water with rapid stirring.

Other precautions must be observed during catalyst preparation if highly selective silver-cadmium alloy compositions are to be achieved. It has beem found that the calcination step of the catalyst preparation is best conducted within narrowly controlled limitations. The calcination step should be accomplished at a temperature between about 175° C and 300° C, and most preferably at a temperature between about 200° C and 250° C. If calcination of a silver-cadmium alloy catalyst is conducted at a temperature above about 300° C, the resultant catalyst exhibits less selectivity for high yield conversion of acrolein to allyl alcohol in the present invention process step (1).

It has also been found that silver-cadmium alloy catalysts are most effective when supported on a carrier substrate, i.e., in combination with an internal diluent. Catalysts prepared without a carrier substrate have been found to have a lower activity and shorter catalyst life than the corresponding supported catalysts in vapor phase hydrogenation of acrolein. A typical carrier substrate will have an initial surface area of more than about 1-10 m²/gm, and an average pore diameter greater than about 20 A. A high proportion of small pores is detrimental to catalyst activity, if the size of the pores are such that capillary condensation of acrolein occurs and causes pore blockage. This results in loss of catalytic activity.

Silver-cadmium alloy catalysts and X-ray diffraction characterization are more fully described in copending patent application Ser. No. 714,201, incorporated herein by reference.

Allyl Alcohol To 4-Hydroxybutanal

The effluent stream from step (1) of the invention process contains a major proportion of allyl alcohol, and minor quantities of propanol and propanal. It is economically advantageous to pass the total product mixture of allyl alcohol, propanol and propanal from step (1) directly into the step (2) reaction zone as a feed stream without separating and removing the propanol and propanal by-product components.

In the practice of step (2) of the invention process, hydrogen and carbon monoxide are contacted under hydroformylation conditions with allyl alcohol at a temperature between about 20° C and 120° C and a pressure between about 15 and 150 psi, preferably in the presence of a hydroformylation catalyst.

In a preferred embodiment of step (2) of the invention process, 4-hydroxybutanal is produced in high yield selectivity by reacting allyl alcohol with hydrogen and carbon monoxide in the presence of a metal-ligand complex hydroformylation catalyst at a temperature between about 20° C and 120° C and a pressure between about 15 and 150 psi. Maintaining the pressure of the hydroformylation system below about 150 psi is an important aspect of step (2) of the present invention process for achieving conversion of allyl alcohol to 4-hydroxybutanal in high yield selectivity.

For the purposes of the present invention it has been found that superior results are achieved if the step (2) hydroformylation reaction is conducted in the presence of a catalyst which is a complex of rhodium metal and a phosphine ligand.

Any of the rhodium-phosphine complexes disclosed in "Carbon Monoxide in Organic Synthesis", Falbe, (Springer-Verlag 1970), pages 22-23, may be used. Preferred catalysts have the formula RhCOH(Q₃P)₃, RhCOH[(QO)₃P]₃, RhCOCl[(QO)₃P]₂ and RhCOCl(Q₃P)₂ wherein Q is phenyl; alkyl phenyl such as tolyl, xylyl, and the like; cyclohexyl; alkyl substituted cyclohexyl such as methyl, propyl, octyl, and the like; substituted cyclohexyl; and aliphatic radical such as methyl, butyl, octyl, and the like; and mixtures of the foregoing, preferably phenyl.

A particularly important aspect of step (2) of the present invention process is based on the discovery that exceptionally high yield of straight chain 4-hydroxybutanal is obtained when the hydroformylation catalyst employed is a complex of rhodium metal, carbon monoxide and triaryl phosphine. Illustrative of this class of catalysts is:

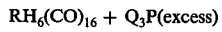

$$RH_6(CO)_{16} + Q_3P(excess)$$

It is to be especially noted that "straight chain selectivity" of product yield is promoted when the molar ratio of triaryl phosphine ligand to rhodium metal in the hydroformylation reaction medium is at least 200 to 1, and preferably at least 400 to 1. Hence, a higher yield of straight chain 4-hydroxybutanal is obtained at the expense of branched chain 2-methyl-3-hydroxypropanal.

Illustrative of a highly preferred embodiment of the present invention, 4-hydroxybutanal is produced in a yield of at least 75 weight percent by reacting allyl alcohol with hydrogen and carbon monoxide in the presence of rhodium carbonyl-triaryl phosphine complex hydroformylation catalyst at a temperature between 70° C and 110° C and a pressure between about 60 and 100 psi. The relative amounts of hydrogen and carbon monoxide employed can vary in accordance with conventional hydroformylation processes, i.e., a molar ratio between 10:1 and 1:10. It has been observed that a higher yield of 4-hydroxybutanal is favored if the ratio of hydrogen to carbon monoxide in the hydroformylation reaction is maintained in the range between about 2:1 and 1:2.

The hydroformylation catalyst is generally employed in a quantity between about 0.01 and 5 weight percent, based on the weight of allyl alcohol starting material, and preferably a weight percent quantity between about 0.1 and 1.0, exclusive of the weight of ligand.

The hydroformylation reaction of the invention preferably is conducted in a solvent, one which is inert with respect to the products or starting materials. The solvent generally dissolves the catalyst, starting material and products. It is convenient and economical to use the feed stream mixture of allyl alcohol, propanol and propanal as the solvent medium. If it is desirable to include an additional solvent component in the system, a wide variety of organic solvents such as, for example, aromatics, aliphatics, esters, ethers, nitriles, alcohols, halogenated hydrocarbons, and the like, including benzene, cyclohexane, ethyl acetate, methyl alcohol, ethyl orthoformate, tetrahydrofuran, dioxane, isopropyl alcohol, aliphatic hydrocarbon cuts (saturated), chlorobenzene, methylene chloride, propionitrile, acetonitrile, trimethyl acetonitrile, and the like, and mixtures thereof may be employed.

For the operation of the present invention step (2) hydroformylation process on a large scale, it is advantageous to employ a rhodium carbonyl catalyst component which is incorporated in a large excess of triaryl phosphine. The said triaryl phosphine can be included in the reaction medium in a quantity which is between 20 and 90 percent of the total weight of catalyst and allyl alcohol reactant. Triphenyl phosphine at a temperatue above about 80° C is highly fluid and performs as an excellent medium for the step (2) hydroformylation process. The highest yields are obtained when triphenyl phosphine is employed as the reaction medium.

Another important advantage of including a solvent as a reaction medium is to insure proper temperature control. Allyl alcohol is highly reactive under hydroformylation conditions, and the solvent performing as a diluent aids in maintaining the reaction rate within controlled limits. It is advantageous to employ a solvent (e.g., triphenyl phosphine or benzene) in a quantity which is at least 50 weight percent of the total reaction mixture, and preferably between about 60–75 weight percent.

The 4-hydroxybutanal which is produced as the high yield product of the step (2) hydroformylation reaction can be separated and recovered in step (3) by conventional distillation procedures. It is highly preferred, however, to subject the hydroformylation product mixture to aqueous phase extraction. Suprisingly it was found that water is capable of extracting 4-hydroxybutanal from the product mixture substantially to the exclusion of the other product mixture components. In a commercial scale operation, an aqueous phase stream can be contacted countercurrently and continuously with reaction product effluent from the step (2) hydroformylation reaction zone. The resultant step (3) aqueous phase containing 4-hydroxybutanal is an excellent vehicle for subsequent processing procedures.

4-Hydroxybutanal To 1,4-Butanediol

The hydrogenation step (4) of the invention process can be conveniently accomplished by hydrogenating an aqueous solution of 4-hydroxybutanal employing conventional catalytic procedures. Suitable hydrogenation catalysts include Raney nickel, copper, cobalt, palladium, platinum, and other catalytically active compositions disclosed in literature such as U.S. Pat. No. 3,284,517. The hydrogenation of 4-hydroxybutanal normally can be conducted at a hydrogen pressure of about 1000–4000 psi and a temperature in the range between about 75° C and 200° C.

Allyl Alcohol Directly To 1,4-Butanediol

In another embodiment, this invention contemplates a process for producing 1,4-butanediol which comprises (1) reacting acrolein with hydrogen in the vapor phase in the presence of a catalyst comprising a silver-cadmium alloy or a carrier substrate, wherein the atomic ratio of silver to cadmium in the alloy is in the range of between about 0.1 and 3 to 1, to yield a hydrogenation product mixture containing allyl alcohol; and (2) contacting the allyl alcohol product mixture with hydrogen and carbon monoxide under hydroformylation conditions in the presence of cobalt metal-ligand complex catalyst to yield a product mixture containing 1,4-butanediol.

For the operation of the step (2) hydroformylation procedure on a large scale, it is advantageous to react the allyl alcohol with hydrogen and carbon monoxide in the presence of a cobalt metal-ligand complex hydroformylation catalyst at a temperature between about 80° C and 120° C and a pressure between about 300 and 3000 psi in a first zone to form 4-hydroxybutanal, and then to pass the reaction stream containing 4-hydroxybutanal into a second zone where it is in contact with the cobalt metal-ligand complex catalyst at a temperature between about 150° C and 225° C and a pressure between about 300 to 3000 psi thereby converting the 4-hydroxybutanal to 1,4-butanediol.

The pressure in the hydroformylation system is preferably between about 1000 and 2000 psi in the first zone, and between about 1000 and 2000 psi in the second zone.

If desired, the hydroformylation can be conducted in a single reactor under constant pressure, wherein the hydroformylation reaction stream passes through the reactor which is maintained with a lower-to-higher temperature gradient. Allyl alcohol converts to 4-hydroxybutanal at the lower temperature end of the reactor, and the 4-hydroxbutanal converts to 1,4-butanediol at the higher temperature end of the reactor.

A preferred type of catalysts for the temperature gradient hydroformylation system for converting allyl alcohol to 1,4-butanediol are cobalt metal hydroformylation catalysts which are phosphine-modified. A suitable catalyst for such a process is a complex of cobalt metal, carbon monoxide and trialkyl phosphine (e.g., tributyl phosphine).

The 1,4-butanediol product of the invention process can be recovered by conventional distillation procedures. The respective reactants and catalysts are recovered and recycled wherever practical, in order to enhance the overall economics of the acrolein to 1,4-butanediol process.

In another embodiment, this invention provides an improved process for producing 1,4-butanediol which comprises (1) reacting acrolein with hydrogen in the vapor phase in the presence of a catalyst comprising a silver-cadmium-zinc alloy, wherein the atomic ratio of silver to cadmium in the alloy is in the range of between about 0.1 and 3 to 1, and the zinc is contained in the alloy in a quantity between about 0.001 and 30 weight percent, based on the total weight of alloy; (2) contacting the allyl alcohol product mixture with hydrogen and carbon monoxide under hydroformylation to yield a product mixture containing 4-hydroxybutanal; (3) separating the 4-hydroxbutanal from the product mixture; and (4) hydrogenating the 4-hydroxybutanal to produce 1,4-buytanediol.

The superior properties of silver-cadmium-zinc alloy, as a catalyst for highly selective hydrogenation of $\alpha,\beta$-unsaturated carbonyl compounds to the corresponding $\alpha,\beta$-unsaturated alcohol derivatives, are more fully described in copending patent application Ser. No. 714,057, incorporated herein by reference.

The following examples are further illustrative of the present invention. The reactants and other specific ingredients are presented as being typical, and various modifications can be derived in view of the foregoing disclosure within the scope of the invention.

Examples I–VI illustrate the high conversion yield of allyl alcohol obtained by hydrogenation of acrolein in the vapor phase over a novel catalyst comprising silver-cadmium alloy on a carrier substrate, in accordance with step (1) of the invention.

Example VII illustrates the invention process step (2) hydroformylation of allyl alcohol to yield 4-hydroxybutanal.

Example VIII illustrates the invention process step (3) hydrogenation of 4-hydroxybutanal to yield 1,4-butanediol.

Example IX illustrates the invention process step (2) modification for direct conversion of allyl alcohol to 1,4-butanediol employing a cobalt catalyst.

EXAMPLE I

A catalyst was prepared by the rapid dropwise co-addition of 100 milliliters of a 1.0 molar $AgNO_3$, 0.49 molar $Cd(NO_3)_2$ solution and 100 milliliters of a 1.72 molar KOH solution to 400 milliliters of vigorously stirred doubly distilled water. About 19 grams of Cab-O-Sil H-5 silica (325 $m^2/g$, Cabot Corp. Boston, Mass.) were then thoroughly mixed with the resultant slurry of silver-cadmium coprecipitate. The slurry was filtered, and the filter cake was wasked with about 600 milliliters of doubly distilled water. The filter cake was calcined in air at 250° C for 16 hours. The resultant material was crushed and screened to yield a 50-80 mesh fraction. Bulk chemical analysis of this meterial indicated that it contained 54% $SiO_2$, 17.3% Cd, 27.5% Ag with 0.3% K also present. Powder X-ray diffraction studies revealed that the composition contained metallic silver crystallites and cadmium oxyhydroxide $Cd_3[O(OH)]_2$ of two types, and cadmium hydroxide $Cd(OH)_2$. The silica, being amorphous, contributed no significant X-ray diffraction pattern.

Approximately 2.62 grams of the prepared silver-cadmium catalyst was charged to a 0.925 cm i.d. by 28 cm reactor tube. Hydrogen gas at 200 psig was passed over the catalyst in the reactor tube at 500 SCCM and the temperature was increased from 21° C to 175° C over the course of 1 hour, at which time the gas was changed to one containing 1 part acrolein and 40 parts hydrogen. The reactor effluent was sampled using a gas sampling valve and gas chromatography. Table I summarizes the process conditions employed and the product yields obtained.

Powder X-ray diffraction examination of the used catalyst disclosed lines at 2.38, 2.06, 1.46 and 1.25 A, which indicated that a silver-cadmium alloy of the α-type was present on the silica. Chemical analysis of the alloy determined the content as 61.4% Ag and 38.5% Cd by weight. No discrete Ag or Cd crystallites were detectable.

EXAMPLE II

A silver-cadmium solution was prepared by dissolving 34 grams $AgNO_3$ (0.020 mole) and 30 grams $Cd(NO_3)_2 \cdot 4H_2O$ (0.097 mole) in doubly distilled water to a total solution volume of 200 milliliters. A sodium hydroxide solution was prepared by dissolving 11.9 grams of NaOH (0.298 mole) in sufficient doubly distilled water to adjust the volume to 200 milliliters. Both solutions were then added dropwise with rapid stirring to 400 milliliters of distilled water. The resultant brown precipitate was recovered and added to a suspension of 100 milliliters of Cab-O-Sil M-5 in 200 milliliters of distilled water with rapid stirring. The suspension was filtered, and the filter cake was washed with 2 liters of distilled water. The moist filter cake was then calcined in air at 250° C for 20 hours. The material was cooled in vacuum desiccator, and then crushed and screened to yield a 50–80 mesh fraction which by bulk chemical analysis was found to contain 61% Ag, 26% Cd and 12% $SiO_2$. Powder X-ray diffraction examination indicated that the silver was present as metallic crystallites and the cadmium was present as CdO.

A quantity of about 7.63 grams of this catalyst precursor was placed in a 0.925 cm i.d. by 28 cm reactor tube and 200 psig hydrogen flowing at 750 SCCM was passed over the catalyst precursor as the temperature was raised from 23° C to 130° C over a period of 36 minutes, at the end of which time the gas was changed to one containing approximately 1 part acrolein to 40 parts hydrogen. Table II summarizes the results obtained under a variety of process conditions with this catalyst.

X-ray diffraction analysis of the used catalyst exhibited strong sharp lines at 2.39, 2.07, 1.46, and 1.25 A with a strong, relatively sharp, back reflection. This indicated an α-phase silver-cadmium alloy on the silica with a composition of 70% Ag and 30% Cd by weight. No discrete silver or cadmium crystallites could be detected by bulk chemical analysis.

TABLE II

| Mole Percent Acrolein In Feed | Catalyst Temp. ° C | Reactor Pressure psig | Contact Time sec. | Weight Percent Acrolein Conversion | Weight Percent Product Selectivity | | |
|---|---|---|---|---|---|---|---|
| | | | | | Allyl Alcohol | Propanal | Propanol |
| 2.1 | 125 | 210 | 9.4 | 12.7 | 46.5 | 49.5 | 4.0 |
| 2.1 | 150 | 214 | 9.6 | 21.2 | 66.2 | 31.5 | 2.3 |
| 2.2 | 175 | 204 | 9.1 | 38.5 | 66.1 | 30.8 | 3.1 |
| 2.2 | 210 | 207 | 5.1 | ≈100 | 70.3 | 0.37 | 29.3 |

EXAMPLE III

For the preparation of a silver-cadmium solution, 34.7 grams $AgNO_3$ (0.204 mole) and 80.0 grams $Cd(NO_3)_2 \cdot 4H_2O$ (0.259 mole) were dissolved in 100 milliliters of distilled water. To this solution was added 17.0 grams of 86.7% KOH (0.263 mole) dissolved in 50 milliliters of distilled water, followed by addition of 400 milliliters of distilled water. The slurry mixture which

TABLE I

| Mole Percent Acrolein In Feed | Catalyst Temp. ° C | Reactor Pressure psig | Contact Time sec. | Weight Percent Acrolein Conversion | Weight Percent Product Selectivity | | |
|---|---|---|---|---|---|---|---|
| | | | | | Allyl Alcohol | Propanal | Propanol |
| 2.2 | 125 | 206 | 7.25 | 2.90 | 73.80 | 26.2 | 0.0 |
| 2.3 | 175 | 198 | 6.97 | 41.42 | 76.20 | 22.0 | 1.8 |
| 0.9 | 175 | 500 | 17.60 | 97.40 | 76.80 | 11.2 | 12.0 | formed was added to 400 milliliters of Cab-O-Sil M-5 suspended in one liter of distilled water with rapid stirring. The resultant solids were filtered off, partially air dried overnight, and calcined in air at 250° C for 16 hours. After cooling in a vacuum desiccator, the material was partially crushed and extracted with distilled water for about 24 hours, then recalcined at 250° C to 300° C for 21 hours in air. The resultant material contained 34% by weight silver, present as metallic crystalllites, 17.9% by weight cadmium hydroxide crystallites of two steps, and 33% by weight of silica, with less than 0.05% K or Cl.

This material was crushed and screened to yield a 50–80 mesh fraction, 3.16 grams of which were loaded into 0.925 cm i.d. by 28 cm reactor tube. Hydrogen gas at 200 psig was passed over the catalyst at 750 SCCM and the temperature brought rapidly from 22° C to 127° C; then the gas was changed to 1 part acrolein in approximately 40 parts hydrogen.

Table III summarizes the results obtained under various conditions employing this catalyst. The reactor effluent stream was analyzed by gas chromatographic techniques. Table III summarizes the reactor conditions, and the analysis of liquid products trapped at −78° C in a collection vessel down stream from the reactor. Bulk chemical analysis of the used catalyst in conjunction with X-ray diffraction scanning indicated that a 62.9% silver and 37.1% cadmium alloy phase was present. Broad X-ray diffraction lines at 2.36, 2.05, 1.45, and 1.23 A along with broad back reflection lines were observed. No discrete silver or cadmium metallic crystallites were detected.

1000 milliliters of Cab-O-Sil M-5 were added, in addition to sufficient water at intervals to maintain mixture fluidity. The final volume was increased to 1800 milliliters. The pH of the supernatant phase was 6.5. Vacuum filtration was employed to produce a filter cake, which was washed with 2000 milliliters of distilled water. The filter cake was calcined in air at 250° C for 25 hours. After cooling in a vacuum desiccator, the catalyst precursor was crushed and screened to yield a 50–80 mesh fraction. Bulk chemical analysis indicated that the catalyst contained 63.7% $SiO_2$, 7.9% Ag, 18.6% Cd and 0.4% K by weight. Powder X-ray diffraction study revealed strong lines due to CdO, and weak lines due to Ag.

About 2.5 grams of this material were charged to a 0.55 cm i.d. by 28 cm reactor tube. Under 197 psig hydrogen flowing at 750 SCCM the temperature was raised from 24° C to 125° C over the course of 1.1 hours, at which time 1 part acrolein in 40 parts hydrogen replaced the pure hydrogen. Table IV lists the reactor conditions and the analysis of the liquid produces collected in a trap held at −78° C under reactor pressure.

X-ray diffraction analysis of the used catalyst indicated the presence of α-phase AgCd and γ-phase AgCd alloys. No discrete metallic cadmium or silver was observed. Lines were observed at 2.41, 2.36, 2.08, A, and a sharp line characteristic of γ at 1.67. The back reflection was weak. Bulk chemical analysis indicated that these alloys had an average composition of 29.8% Ag and 70.2% Cd.

TABLE IV

| Mole Percent Acrolein In Feed | Catalyst Temp. ° C | Reactor Pressure psig | Contact Time sec. | Weight Percent Acrolein Conversion | Weight Percent Product Selectivity | | |
|---|---|---|---|---|---|---|---|
| | | | | | Allyl Alcohol | Propanal | Propanol |
| 2.30 | 125 | 197 | 6.1 | 12 | 73 | 21 | 1 |
| 2.30 | 150 | 198 | 6.1 | 14 | 74 | 26 | 0 |
| 2.20 | 175 | 201 | 6.2 | 8 | 74 | 26 | 0 |
| 0.89 | 125 | 505 | 7.8 | 7 | 77 | 23 | 0 |
| 0.89 | 150 | 506 | 7.8 | 11 | 77 | 22 | 0 |
| 0.88 | 175 | 512 | 7.9 | 33 | 77 | 17 | 2 |
| 0.87 | 185 | 516 | 8.0 | 54 | 73 | 21 | 3 |

TABLE III

| Mole Percent Acrolein In Feed | Catalyst Temp. ° C | Reactor Pressure psig | Contact Time sec. | Weight Percent Acrolein Conversion | Weight Percent Product Selectivity | | |
|---|---|---|---|---|---|---|---|
| | | | | | Allyl Alcohol | Propanal | Propanol |
| 2.1 | 125 | 209 | 7.8 | 38.5 | 68.0 | 31.0 | 0.0 |
| 2.0 | 150 | 223 | 8.3 | 84.7 | 69.5 | 28.0 | 2.0 |

TABLE IIIA

| 2.2 | 150 | 206 | 7.7 | 78.0 | 69.0 | 28.0 | 3.0 |
| 1.6 | 170 | 290 | 5.2 | 99.9 | 66.0 | 24.0 | 10.0 |
| 0.9 | 156 | 485 | 9.7 | 97.0 | 71.0 | 19.0 | 9.0 |
| 0.9 | 160 | 515 | 10.3 | 99.9 | 70.0 | 13.0 | 17.0 |

EXAMPLE IV

A solution was prepared by dissolving 13.07 grams $AgNO_3$ (0.077 mole) and 37.97 grams $Cd(NO_3)_2 \cdot 4H_2O$ (0.123 mole) in 100 milliliters of distilled water. A second solution was prepared by dissolving 20.75 grams of KOH in distilled water. Both solutions were then rapidly and simultaneously added to a vigorously stirred 100 milliliters of distilled water, and the resulting precipitate was further suspended by the addition of 500 milliliters of distilled water. After 1 hour of stirring,

EXAMPLE V

A solution of 34.1 grams $AgNO_3$ (0.20 mole) and 60.2 grams $Cd(NO_3)_2 \cdot 2H_2O$ (0.195 mole) in 200 milliliters of water was added simultaneously with a solution of 34.95 grams of 87.4% analytical reagent grade KOH (0.591 mole) in 200 milliliters of water to 400 milliliters of rapidly stirred distilled water. The pH of the supernatant phase after addition was 6.0. The volume of the suspension was increased to 1500 milliliters, and 1000 milliliters of Cab-O-Sil M-5 were added with vigorous stirring. The total volume was adjusted to 2000 milliliters and the slurry was filtered. The filter cake was washed with 3000 milliliters of distilled water, calcined in air at 250° C for 215 hours, and the resulting catalyst precursor was crushed and screened to yield a 50–80 mesh fraction. Chemical analysis indicated that the composition contained 49.6% $SiO_2$, 25.9% Ag, 18.6% Cd, and 0.4% K. Powder X-ray diffraction indicated that metallic silver and cadmium oxide, CdO, both of medium order were present at this stage, besides the amorphous $SiO_2$ which did not contribute detectable X-ray diffraction lines.

A 7.35 grams quantity of this catalyst precursor were placed in a 0.925 cm i.d. by 28 cm reactor tube. Under 499 psig hydrogen flowing at 1500 SCCM, the reactor was heated to 200° C from 18° C, maintained at 200° C for 15 minutes, and cooled to 125° C over a total period of one hour. The hydrogen was then replaced by 1 part acrolein in 111 parts hydrogen. Table V summarizes the results based on the analysis of liquid products collected at −78° C under reactor pressure.

A 2.71 gram quantity of the catalyst precursor was placed in a 0.55 cm i.d. by 28 cm reactor tube, and under 620 psig hydrogen flowing at 1500 SCCM the material was heated from 10° C to 200° C over a period of 1 hour. The catalyst was maintained at 200° C for 15 minutes and then cooled rapidly to 125° C, at which time an acrolein/hydrogen stream replaced the pure hydrogen. Table V summarizes various reactor conditions and the composition of the liquid products collected in a trap held at −78° C and reactor pressure.

X-ray diffraction analysis of the used catalyst indicated that the principal AgCd alloy was the α-phase with some γ-phase also present. Bulk chemical analysis indicated that the average composition of the silver cadmium alloy on silica was 58.2% Ag and 41.8% Cd.

EXAMPLE VI

A 28.77 gram quantity of analytical reagent grade KOH (0.446 mole) was added to 200 milliliters of distilled water, and the resultant solution was warmed to 100° C. With rapid stirring a solution of 25.26 grams $AgNO_3$ (0.149 mole) and 45.85 grams $Cd(NO_3)_2 \cdot 4H_2O$ (0.149 mole) in 100 milliliters of distilled water was added. The suspension was cooled and diluted by the addition of 1000 milliliters of 2° C distilled water followed by 100 milliliters of Cab-O-Sil M-5. Additional distilled water was added to adjust the total volume to 1800 milliliters. The pH of the supernatant phase was 6.5.

The suspension was vacuum filtered, and the filter cake was washed with 2000 milliliters of distilled water and calcined in air at 250° C for 20 hours. The catalyst precursor was then crushed and screened to provide a 50–80 mesh fraction. X-ray diffraction examination revealed principally CdO of medium order, and no detectable silver lines.

A 4.04 gram quantity of this material was placed in a 0.55 cm i.d. by 28 cm reactor tube. The reactor under 490 psig hydrogen flowing at 1500 SCCM was heated from 20° C to 200° C, held at 200° C for 15 minutes and cooled to 125° C over the course of 1.6 hours. At this time, the hydrogen was replaced by 1 part acrolein in 109 parts hydrogen. Table VI summarizes various reactor conditions, and the resultant composition of liquid products collected in a trap held at −78° C and reactor pressure. The used catalyst, 5.7% silica with 65.7% alloys, consisted of well ordered α,γ and some ε-phase AgCd alloy on $SiO_2$. The average alloy composition was 52.4% Ag and 46.6% Cd.

TABLE VI

| Mole Percent Acrolein In Feed | Catalyst Temp. ° C | Reactor Pressure psig | Contact Time sec. | Weight Percent Acrolein Conversion | Weight Percent Product Selectivity | | |
|---|---|---|---|---|---|---|---|
| | | | | | Allyl Alcohol | Propanal | Propanol |
| 0.91 | 125 | 494 | 7.9 | 8.95 | 69.2 | 18.0 | 4.4 |
| 0.89 | 150 | 503 | 8.1 | 10.80 | 77.7 | 19.3 | 1.0 |
| 0.89 | 175 | 506 | 8.1 | 55.00 | 78.7 | 12.8 | 9.8 |
| 0.89 | 190 | 506 | 8.1 | 97.60 | 70.9 | 5.1 | 23.1 |
| 0.91 | 200 | 496 | 7.9 | 99.10 | 61.2 | 2.7 | 35.7 |

EXAMPLE VII

TABLE V

| Mole Percent Acrolein In Feed | Catalyst Temp. ° C | Reactor Pressure psig | Contact Time sec. | Weight Percent Acrolein Conversion | Weight Percent Product Selectivity | | |
|---|---|---|---|---|---|---|---|
| | | | | | Allyl Alcohol | Propanal | Propanol |
| 0.90 | 125 | 502 | 18.7 | 61.0 | 72 | 15 | 11 |
| 0.89 | 150 | 504 | 18.8 | 82.0 | 76 | 14 | 8 |
| 0.89 | 175 | 501 | 18.7 | 99.4 | 66 | 3 | 31 |
| 0.90 | 180 | 502 | 18.7 | 99.7 | 68 | 1 | 31 |

Allyl alcohol (10 grams), benzene (40 grams), triphenyl phosphine (30 grams) and hexarhodium hexa-

TABLE V-A

| Mole Percent Acrolein In Feed | Catalyst Temp. ° C | Reactor Pressure psig | Contact Time sec. | Weight Percent Acrolein Conversion | Weight Percent Product Selectivity | | |
|---|---|---|---|---|---|---|---|
| | | | | | Allyl Alcohol | Propanal | Propanol |
| 3.00 | 150 | 999 | 6.7 | 11.1 | 78.9[1] | 21.1 | 0.0 |
| 3.00 | 175 | 999 | 6.7 | 91.3 | 74.2[2] | 15.5 | 10.3 |

Sty (Grams Allyl Alcohol/Liter Hour)
[1] 103
[2] 958 decyl carbonyl (0.05 grams) were sealed in a 300 ml "Magnadrive" autoclave. The vessel was pressured with carbon monoxide to 90 psig and depressurized twice then heated to 80° C. A mixture of carbon monoxide and hydrogen (1:1 mole ratio) was admitted to the vessel until the pressure reached 90 psig. Constant gas pressure was maintained on the reaction vessel by means of a pressure regulator attached to a one liter storage vessel also containing a mixture of carbon monoxide and hydrogen (1:1 mole ratio). Gas absorption ceased after 40 minutes. The reactor was cooled to room temperature and the liquid contents analyzed by gas chromatography. The allyl alcohol conversion was found to be 99% to 4-hydroxybutanal (87 wt%), 2-methyl-3-hydroxypropanal (12 wt%) and propanal (1 wt%).

EXAMPLE VIII

The liquid contents from Example VII were extracted with two 25 ml portions of water. A gas chromatograph of the benzene/triphenyl phosphine/rhodium carbonyl showed only traces of aldehydes indicating quantitative extraction of the products by water. These aqueous extracts were combined (59 grams) and hydrogenated with Raney nickel (1.0 gram) at 110° C for 2 hours under 1000 psig hydrogen pressure in a "Magnadrive" autoclave. Gas chromatographic analysis of the resulting liquid showed 99% conversion to a mixture of 1,4-butanediol and 2-methyl-1,3-propanediol.

EXAMPLE IX

In the same manner Example VII, allyl alcohol (10 grams) benzene (40 grams), tributyl phosphine (50 grams) and dicobalt octa carbonyl (0.1 gram) are sealed in a 300 ml "Magnadrive" autoclave. The vessel is pressurized to 300 psig with a mixture of carbon monoxide and hydrogen (1:1 mole ratio), and the gas pressure is held constant while the hydroformylation reaction medium is maintained at a temperature of 100° C for 1 hour.

The temperature is then increased to 200° C and maintained until the conversion of the 4-hydroxybutanal intermediate to 1,4-butanediol is completed.

Similar results are obtained for conversion of acrolein to 1,4-butanediol when a silver-cadium-zinc alloy is employed in place of silver-cadmium alloy as a hydrogenation catalyst in step (1) of the invention process.

What is claimed is:

1. A process for producing 1,4-butanediol which comprises (1) reacting acrolein with hydrogen in the vapor phase in acrolein/hydrogen molar ratio between 1:1 and 1:1000 at a temperature between about 75° C and 250° C and a pressure between about 75 and 5000 psi in the presence of a catalyst comprising a silver-cadmium alloy to yield a hydrogenation product mixture containing alcohol, wherein the automic ratio of silver to cadmium in the alloy is in the range of between about 0.1 and 3 to 1, and the alloy exhibits an X-ray diffraction pattern which is substantially free of detectable unalloyed metal crystallite lines; (2) contacting the allyl alcohol product mixture with hydrogen and carbon monoxide in a hydrogen carbon monoxide ratio between 1:2 and 2:1 under hydroformylation conditions at a temperature between about 20° C and 120° C and a pressure between about 15 and 150 psi in the presence of a hydroformylation catalyst to yield a product mixture containing 4-hydroxybutanal; (3) separating the 4-hydroxybutanal from the product mixture; and (4) hydrogenating the 4-hydroxybutanal to product 1,4-butanediol.

2. A process in accordance with claim 1 wherein the silver-cadmium alloy in step (1) is supported on a carrier substrate.

3. A process in accordance with claim 18 wherein the carrier substrate is silica.

4. A process in accordance with claim 1 wherein in step (2) the hydrogen and carbon monoxide are in a molar ratio between about 1:2 and 2:1.

5. A process in accordance with claim 1 wherein in step (2) the hydroformylation catalyst is a complex of rhodium metal and phosphine ligand.

6. A process in accordance with claim 1 wherein in the step (2) hydroformylation reaction the allyl alcohol is converted to 4-hydroxybutanal in a yield of at least 75 weight percent.

7. A process in accordance with claim 1 wherein in step (3) the separation of 4-hydroxybutanal from the product mixture is achieved by aqueous extraction of the product mixture.

8. A process in accordance with claim 7 wherein in step (3) the 4-hydroxybutanal product is separated from the reaction mixture by aqueous extraction, and the resultant aqueous extract phase is subjected to hydrogenation conditions in step (4) to convert 4-hydroxybutanal to 1,4-butanediol.

9. A process for producing 1,4-butanediol which comprises (1) reacting acrolein with hydrogen in the vapor phase at a temperature between about 75° C and 250° C and a pressure between about 75 and 5000 psi in the presence of a catalyst comprising a silver-cadmium alloy on a carrier substate to yield a hydrogenation product mixture containing allyl alcohol, wherein the atomic ratio of silver to cadmium in the alloy is in the range of between about 0.1 and 3 to 1, and the alloy exhibits an X-ray diffraction pattern which is substantially free of detectable unalloyed metal crystallite lines; and (2) contacting the allyl alcohol product mixture with hydrogen and carbon monoxide under hydroformylation conditions in the presence of cobalt metal-ligand complex catalyst to yield a product mixture containing 1,4-butanediol.

10. A process in accordance with claim 9 wherein in step (2) the hydroformylation reaction is conducted in series at a temperature between about 80° C and 120° C and a pressure between about 300 and 3000 psi in a first zone, and a temperature between about 150° C and 225° C and a pressure between about 300 and 3000 psi in a second zone.

11. A process for producing 1,4-butanediol which comprises (1) reacting acrolein with hydrogen in the vapor phase at a temperature between about 75° C and 250° C and a pressure between about 75 and 5000 psi in the presence of a catalyst comprising a silver-cadmium-zinc alloy to yield a hydrogenation product mixture containing allyl alcohol, wherein the atomic ratio of silver to cadmium in the alloy is in the range of between about 0.1 and 3 to 1 and the zinc is contained in the alloy in a quantity between about 0.001 and 30 weight percent based on the total weight of alloy, and the alloy exhibits and X-ray diffraction pattern which is substantially free of detectable unalloyed metal crystallite lines; (2) contacting the allyl alcohol product mixture with hydrogen and carbon monoxide under hydroformylation to yield a product mixture containing a 4-hydroxybutanal; (3) separating the 4-hydroxybutanal from the product mixture; and (4) hydrogenating the 4-hydroxybutanal to product 1,4-butanediol.

12. A process in accordance with claim 11 wherein the silver-cadmium-zinc alloy in step (1) is supported on a carrier substrate.

* * * * *